US009101837B1

(12) United States Patent
Snyder et al.

(10) Patent No.: US 9,101,837 B1
(45) Date of Patent: *Aug. 11, 2015

(54) ONLINE GAME TO PROMOTE PHYSICAL ACTIVITY

(71) Applicant: Humana Inc., Louisville, KY (US)

(72) Inventors: Seth Snyder, Providence, RI (US); Jasper Speicher, Oakland, CA (US)

(73) Assignee: Humana Inc., Louisville, KY (US)

( * ) Notice: Subject to any disclaimer, the term of this patent is extended or adjusted under 35 U.S.C. 154(b) by 43 days.

This patent is subject to a terminal disclaimer.

(21) Appl. No.: 13/965,701

(22) Filed: Aug. 13, 2013

Related U.S. Application Data

(63) Continuation of application No. 12/756,390, filed on Apr. 8, 2010, now Pat. No. 8,506,396.

(60) Provisional application No. 61/168,313, filed on Apr. 10, 2009.

(51) Int. Cl.
*G06F 17/00* (2006.01)
*A63F 13/212* (2014.01)
*A63F 1/12* (2006.01)

(52) U.S. Cl.
CPC .............. *A63F 13/212* (2014.09); *A63F 1/12* (2013.01); *A63F 2300/1012* (2013.01)

(58) Field of Classification Search
CPC .............. A63F 2300/5566; A63F 2300/5553; A63F 2300/558; A63F 2300/8005; A63F 2300/1012; A63F 13/795; A63F 13/798; A63F 13/816; A63F 13/50; A63F 13/212
See application file for complete search history.

(56) References Cited

U.S. PATENT DOCUMENTS

| | | | |
|---|---|---|---|
| 2006/0141431 A1* | 6/2006 | Lee | 434/236 |
| 2007/0173323 A1* | 7/2007 | Johnson et al. | 463/42 |
| 2008/0146334 A1* | 6/2008 | Kil | 463/36 |
| 2009/0144639 A1* | 6/2009 | Nims et al. | 715/757 |
| 2009/0300513 A1* | 12/2009 | Nims et al. | 715/747 |
| 2010/0115426 A1* | 5/2010 | Liu et al. | 715/757 |
| 2011/0248992 A1* | 10/2011 | van Os et al. | 345/419 |

OTHER PUBLICATIONS iPhone. Wikipedia.org. Online. Accessed via the Internet. Accessed Apr. 2, 2012. <URL http://en.wikipedia.org/wiki/iPhone>.*

\* cited by examiner

*Primary Examiner* — Paul A D'Agostino
*Assistant Examiner* — Carl V Larsen
(74) *Attorney, Agent, or Firm* — Standley Law Group LLP

(57) ABSTRACT

An online game that promotes physical activity by visually representing the comparative biometric data of a group of people. The biometric data may be collected using a variety of biometric devices. Each individual in the group selects an avatar for use in representing the biometric data. The biometric data is transmitted to a server and displayed collectively on a computer screen. Each individual's avatar is displayed on the screen and animated according the biometric data. In an example embodiment in which avatars are fish that are displayed on a fish tank background and the biometric data is steps counted by a pedometer, avatars associated with individuals having a higher step count are positioned above avatars for individuals having a lower step count. Biometric data may be collected from biometric devices at various time intervals and the display updated to reflect the changes in biometric data.

20 Claims, 14 Drawing Sheets

ONLINE GAME TO PROMOTE PHYSICAL ACTIVITY

CROSS-REFERENCE TO RELATED APPLICATIONS

This application claims priority to U.S. Provisional Application Ser. No. 61/168,313, filed Apr. 10, 2009, titled ONLINE GAME TO PROMOTE PHYSICAL ACTIVITY, and to U.S. application Ser. No. 12/756,390, filed Apr. 8, 2012, titled ONLINE GAME TO PROMOTE PHYSICAL ACTIVITY, now U.S. Pat. No. 8,506,396, issued Aug. 13, 2013, the contents of which are incorporated by reference as if fully recited herein.

FIELD OF THE INVENTION

The present invention relates to computerized games that encourage healthy habits among users. In particular, the present invention relates to a computerized game that provides a visual representation of the comparative activity levels of users in a fun and entertaining way.

BACKGROUND OF THE INVENTION

Across the different age categories of our society, obesity is on the rise. Also on the rise are the health complications that obesity causes, such as diabetes, heart disease, hypertension, and stroke. Obesity is often caused or furthered by a sedentary lifestyle. Television watching, video-game playing, and computer use are all things that can cause too little exercise in one's life. Children may gain unnecessary pounds when they spend too much time in front of the television, and adults may gain unwanted pounds due to sitting behind a desk all day.

For those people who wish to become more active it can be difficult to measure one's activity level on a day to day basis. This is especially true if one's desire is to simply incorporate more walking into their daily routine. This is one reason why pedometers are widely available in the marketplace and allow people to keep track of how many steps they take each day.

However, even with a pedometer motivation to stay active can lessen or cease over time, which means that it is especially important for anyone who wishes to become more active to have a continuous source of motivation. It is important that whenever possible physical activity have an element of fun to it, since people are more likely to be physically active when they perceive it as being fun and not simply exercise. Friendly competition is another thing that can motivate people to be more physically active. Also, since people tend to enjoy playing computer games, incorporating a computer game element into a physical activity can make an activity even more enjoyable and increase motivation to continue with the activity. Also, a game that supports multiple players and allows individuals to play against each other is even more likely to keep people motivated. Therefore, there is a need for a game that can allow people to keep track of and compare their physical activity with one another in order to provide friendly competition and motivation to do more activity. There is also a need for a game that is on-line so that it can be accessed from multiple computers, and therefore more convenient for a user to play the game. There is also a need for a game that makes it easy for users to upload their activity data into the system. There is also a need for a fun and entertaining way of visually representing users and their activity levels in the game, and a way for users to customize their game experience.

SUMMARY OF THE INVENTION

The present invention is an online game that promotes physical activity by visually representing the comparative biometric data of a group of people. The biometric data may be collected using a variety of biometric devices such as pedometers, glucometers, weight scales, etc. Each individual in the group selects an avatar for use in representing his or her biometric data. The biometric data is transmitted to a server and displayed collectively on a computer screen. Each individual's avatar is displayed on the screen and animated according the individual's biometric data. In an example embodiment in which avatars are fish that are displayed on a fish tank background and the biometric data is steps counted by a pedometer, avatars associated with individuals having a higher step count may appear in different part of the tank than avatars for individuals having a lower step count. For example, avatars with a higher level of biometric data may be positioned above avatars with a lower level of biometric data. In other embodiments, the speed of the avatars may be varied according to levels of biometric data.

A variety of avatars and backgrounds may be used to represent the comparative data. Biometric data may be collected from biometric devices at various time intervals (e.g., hourly, daily, weekly) and the display may be updated to reflect the changes in biometric data. The individuals in the group can see how their biometric data compares the data of other members in the group by viewing the changes in the display. A variety of visual representations may be used (e.g., speed, size, location) to reflect the relative biometric data values. The ability to see comparative visual representations allows the group to engage in healthy competition to have the best biometric data.

DETAILED DESCRIPTION

In one exemplary embodiment an on-line game provides visual representations of the number of steps game users have taken as reported by pedometers that the users are wearing.

Figure 1:
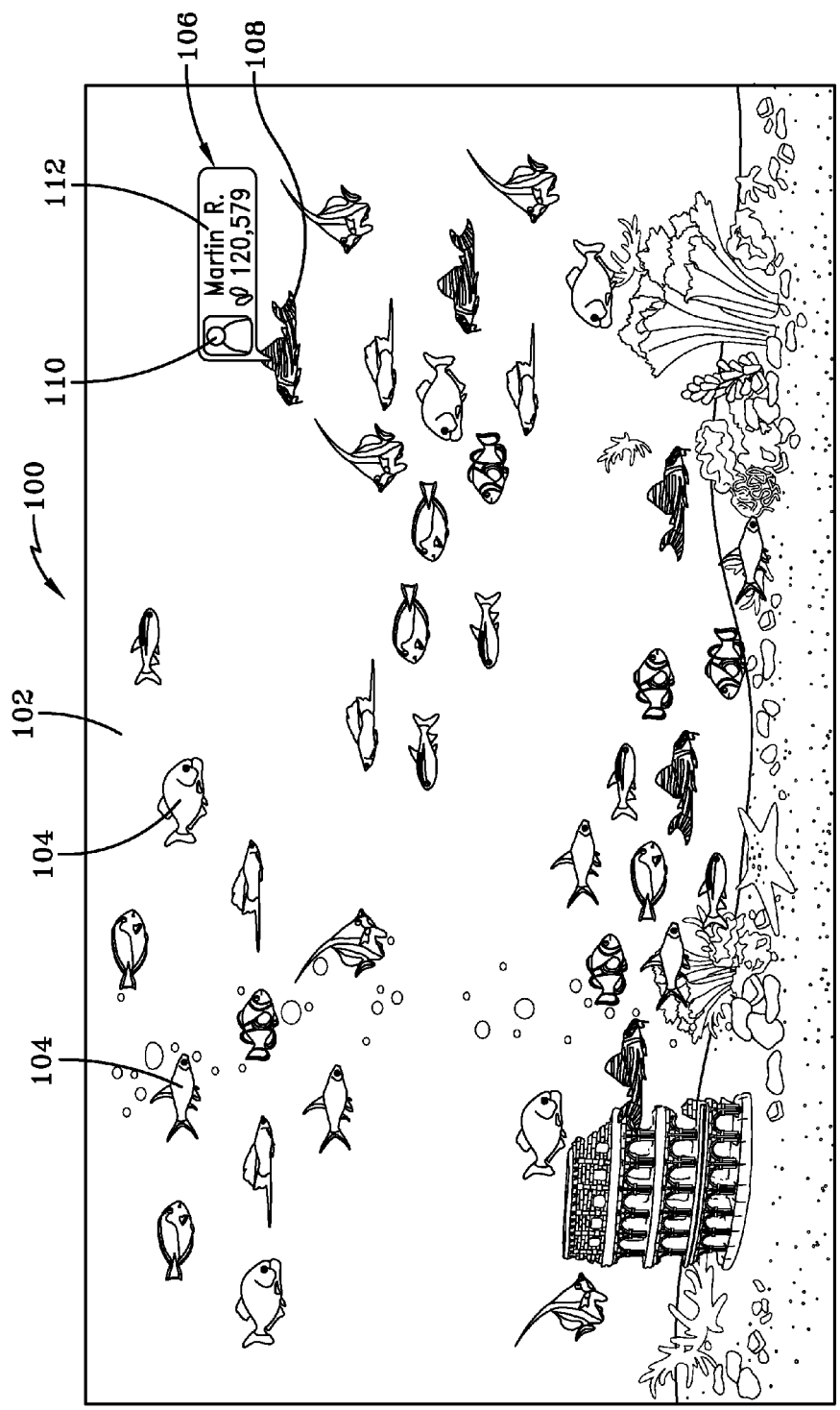
FIG. 1 is a sample main tank page according to an example embodiment.

Referring to FIG. 1, a sample main tank page according to an example embodiment is shown. The main tank page elements include a fish tank 100 that has a background image 102, and multiple fish avatars 104 that are comprised of different types of fish and are located throughout the tank 100. Each avatar 104 represents a different user of the game. The fish avatars 104 in FIG. 1 are animated and move around the tank 100 in such as way as to simulate swimming.

In some embodiments someone observing the fish tank on a touch screen can tap an avatar 104 to find out more about the person it represents. In these embodiments, when an avatar 104 is tapped, an on-screen tag 106 appears near the avatar 104 that shows information about the avatar 104 and the person that the avatar 104 represents. As shown in FIG. 1, an avatar 104 in the form of a catfish 108 has been tapped and the tag 106 shows a profile picture 110 of the user and the user's name 112, which in FIG. 1 is "Martin R." The tag 106 also shows activity level information 114, which in this example is that Martin R. has taken 120,579 steps. In other embodiments, user information different from that shown in FIG. 1 may be shown on the tags 106. For example, in embodiments played by users in a work office environment, the tags 106 may show the professional title of a user or the department they work in. In other embodiments different information may appear on the tags 106. When a user is viewing the tank 100 on a screen that is not a touch screen, an avatar tag 106 may be viewed by clicking a mouse over the avatar 104 or otherwise selecting the avatar 104.

Figure 2:
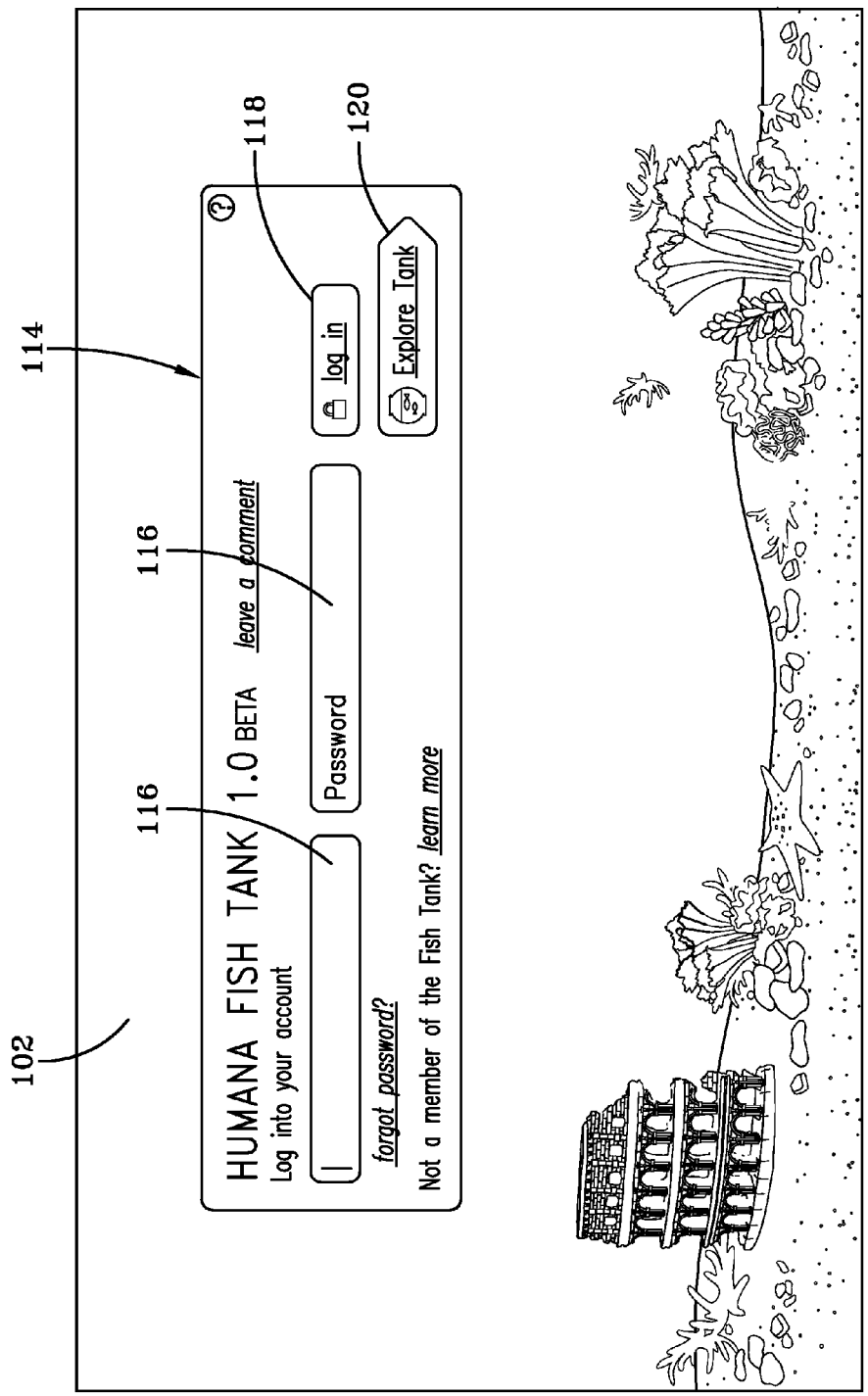
FIG. 2 is a sample log-in page according to an example embodiment.

Referring to FIG. 2, a sample user log-in page according to an example embodiment is shown. The log-in page elements include a background image 102 that is the same as that in FIG. 1, and a log-in section 114. The log-in section 114 contains two text boxes 116 for entering a user's log-in name and password. The log-in section 114 also includes a button a user may select to log in once a user has entered their log-in information 118 and a button that routes the user to the main tank page 120.

Figure 3:
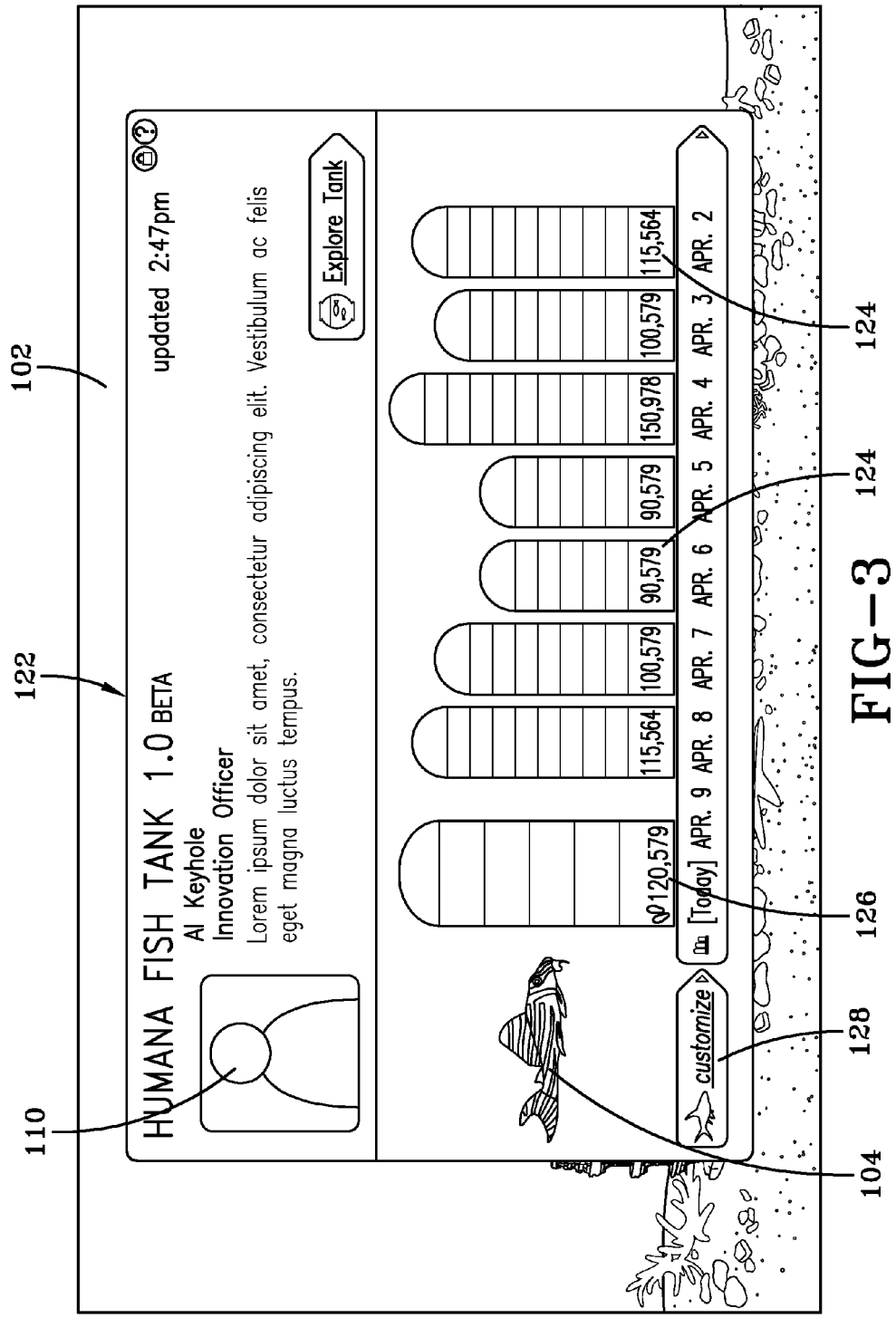
FIG. 3 is a sample fitness profile page according to an example embodiment.

Referring to FIG. 3, a sample fitness profile page according to an example embodiment is shown. The fitness profile page elements include a background image 102 that is the same as FIGS. 1 and 2, and a fitness profile section 122. The fitness profile section 122 contains the profile picture 110 of the user and an image of the user's avatar 104. The fitness profile section 122 also contains visual representations of the user's daily activity levels 124. In FIG. 3 the current daily activity level and the past seven daily activity levels are shown, but in other embodiments different time frames of daily activity levels 124 may be shown. Also, in some embodiments the user may be able to access past daily activity level data that is no longer shown. In FIG. 3 the daily activity levels 124 are represented as vertical bars 126 with heights that correspond to the number of steps the user took on a particular day. The number of steps taken each day is printed on each bar 126. The daily activity levels 124 include the activity level of the current day, which in this example is April 9$^{th}$, and the number of steps taken on April 9$^{th}$ is 120,579. In other embodiments the daily activity levels 124 may be visually represented in different ways. The fitness profile section 122 contains an explore tank button 120 for routing the user to a main tank page, and also contains a customize button 128 that routes the user to a page where they can select their avatar 104. The fitness profile section may also contain additional information about the user, including their name and job information.

Figure 4:
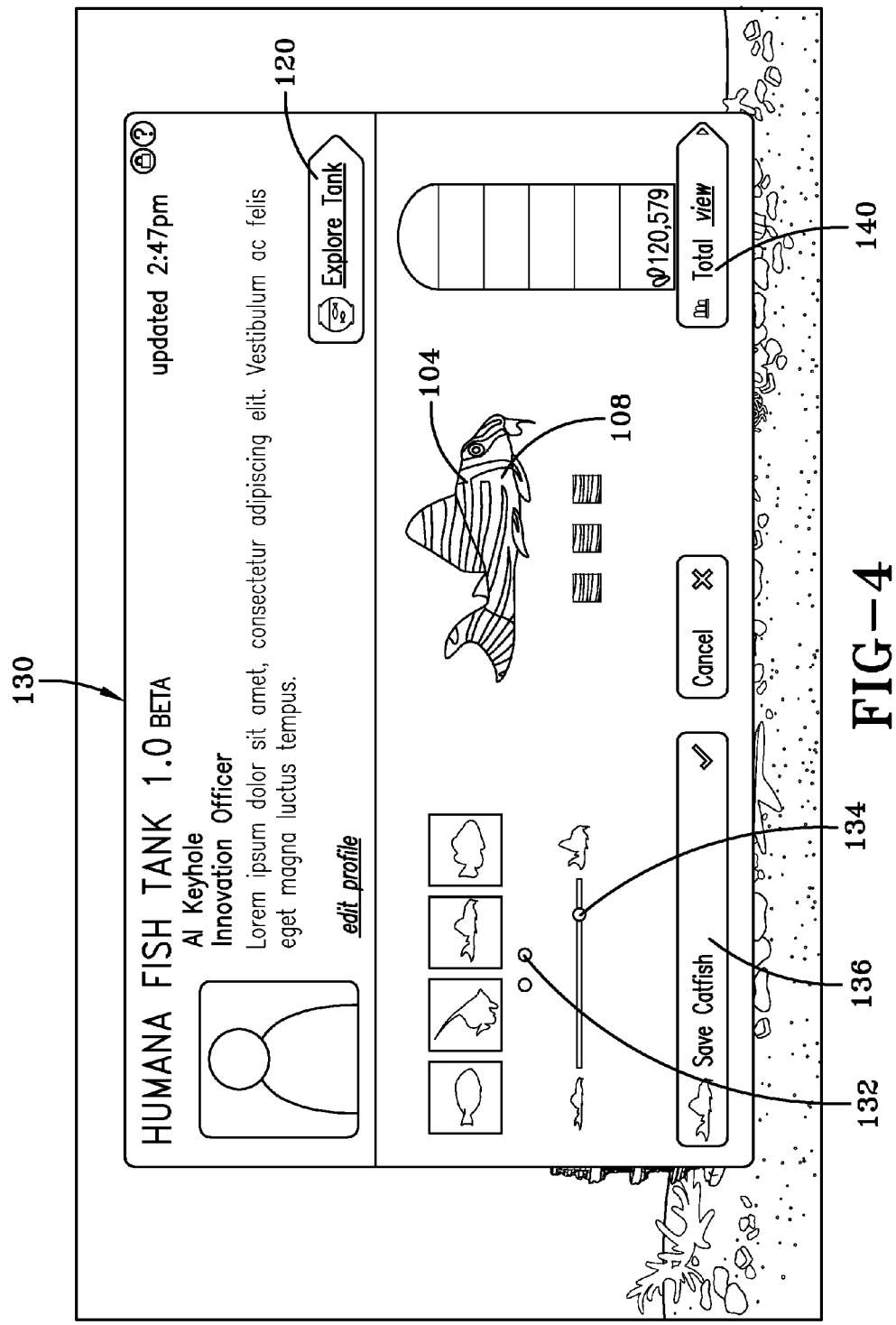
FIG. 4 is a sample avatar selection page according to an example embodiment.

Referring to FIG. 4, a sample avatar selection page according to an example embodiment is shown. The avatar selection page elements include a background image 102 that is the same as FIGS. 1, 2, and 3, and an avatar selection section 130. The avatar selection section 130 contains the profile picture 110 of the user, as well as a picture of their current avatar 104, which in FIG. 3 is a catfish 108. Toggle buttons 132 allow the user to select which fish they want, and a sliding button 134 allows the user to select how thick they want their avatar to be. Beneath the picture of the avatar 104, different color options for the avatar are also presented. Buttons allow the user to save their current avatar selection or cancel it. An explore tank button 120 is also included in the avatar selection section 130, as well as a button for routing the user to the fitness profile page 140 and an activity level bar 126 showing the current day's activity level 124. The avatar selection section also includes a link for editing the user's profile 142.

Figure 5:
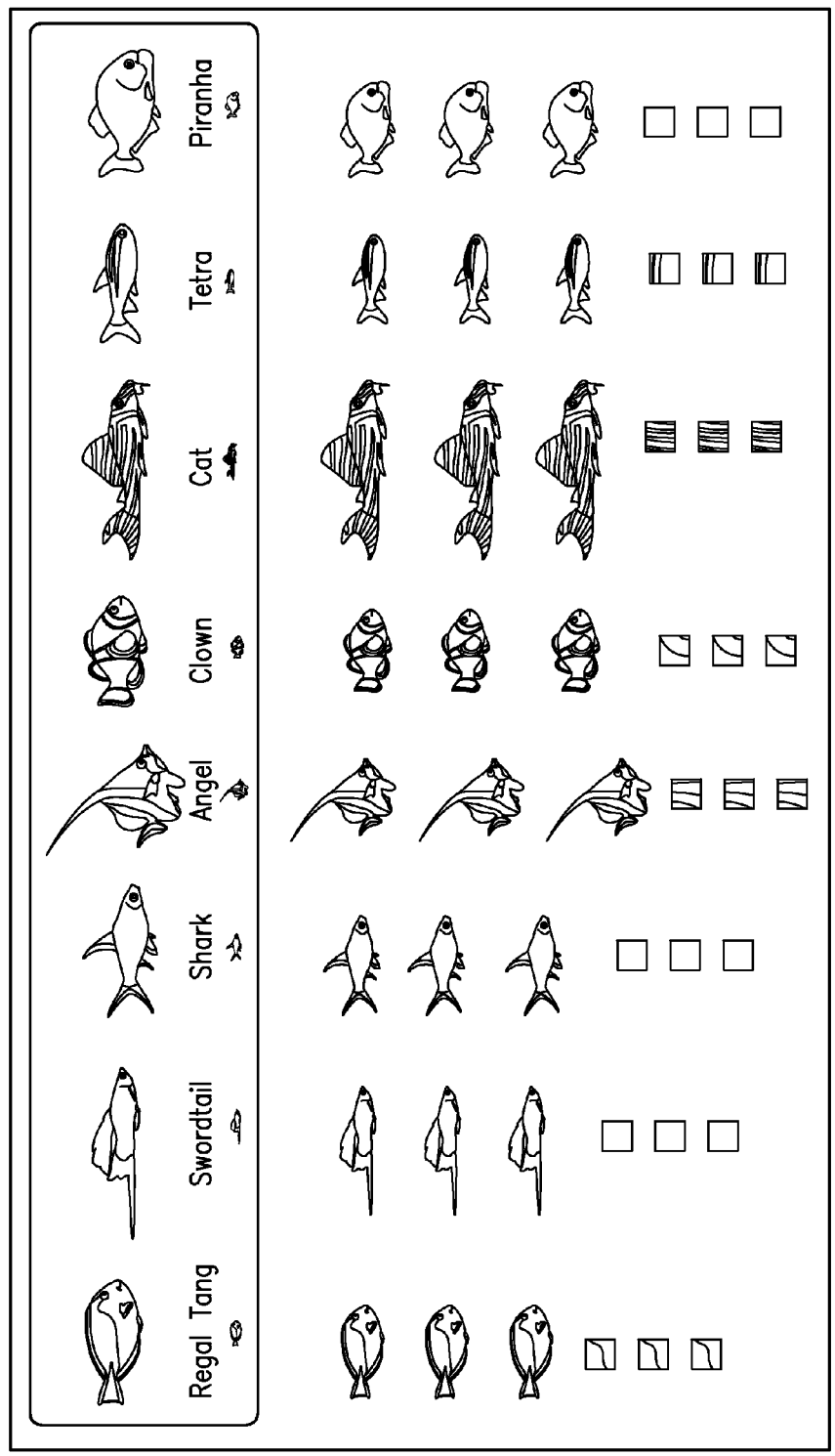
FIG. 5 is a sample avatar profile page according to an example embodiment.

Referring to FIG. 5, a sample avatar profile page according to an example embodiment is shown. This page allows the user to view the different types of avatars 104 available in the game and determine the avatar 104 and color by which they wish to be represented in the fish tank 100. In this embodiment, the different avatar types are as follows: regal tang; swordtail; shark; angel fish; clown fish; catfish; tetra; and piranha. Each type of avatar 104 is available in three different types of colors. In other embodiments different avatars may be available for user selection, whether they are different kinds of fish, or different types of animals or people. The options to change an avatar's visual characteristics such as color and size may vary as well.

Figure 6:
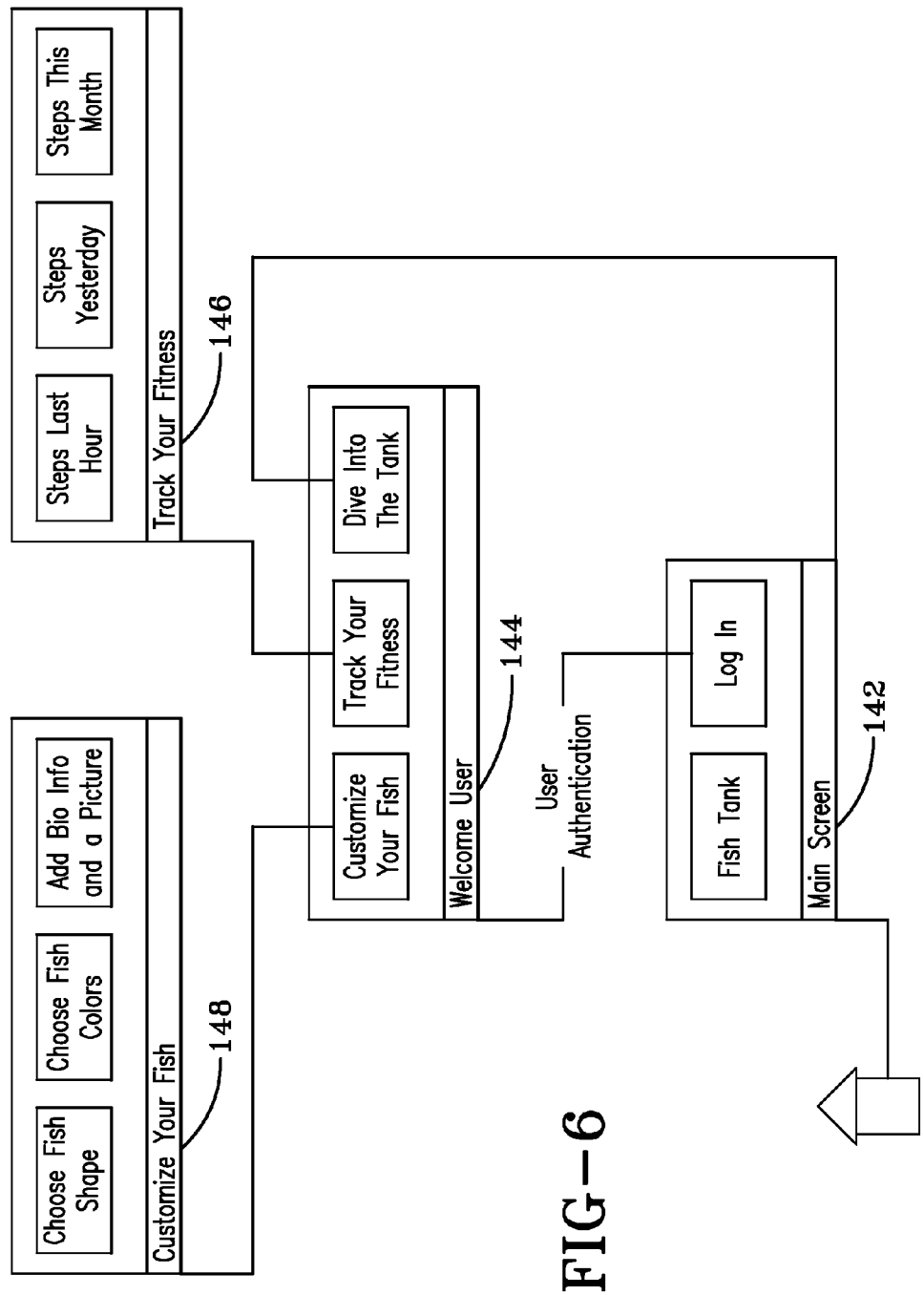
FIG. 6 is a sample game page layout diagram according to an example embodiment.

Referring to FIG. 6, a sample game page layout diagram according to an example embodiment is shown. In this layout, when a user first enters the game they come to a main screen 142 where they can view the fish tank 100 and log into the game. Once the system has authenticated the user, they can view a welcome user screen 144 that offers them the options of customizing their avatar 104, tracking their fitness, or viewing the fish tank 100. If they wish to review their activity levels they can go to a "Track Your Fitness" screen 146 where they can view the steps they have taken in the last hour, the steps they took the day before, or the number of steps they have taken in the past month. If they wish to customize their fish, then they are taken to a customization screen 148 where they are able to choose their fish shape, choose the colors for their fish, or add biographical information and upload a picture to be part of their profile. Different embodiments may have different game layouts than that presented in FIG. 6, and may have more or fewer game pages. For example, in some embodiments a user may be routed directly to the fish tank from any web page. Also, in different embodiments different page layouts may be used in order to provide additional options for customizing the user's experience, recording activity data, viewing the fish tank, or reporting activity data.

In an exemplary embodiment the on-line game is played by users who share a common characteristic, such as working at the same office or in the same building. In such an embodiment the users can view the pages of the game on-line through a web application, so that the game can be accessed from any computer that has internet. If the game is only played by users who have computers that are all on a shared network, then the internet may not be necessary for facilitating the game. In some embodiments a touch screen may also be dedicated to showing the fish tank and allowing users to interact with the game via its touch screen. In other embodiments, a live display of the fish tank on a computer or TV screen may otherwise be available for viewing and interaction by users of the game. Also, while the game may be played by multiple persons in the same office or building, due to the web application it may also be played among persons who are at a distance from each other.

Figure 7:
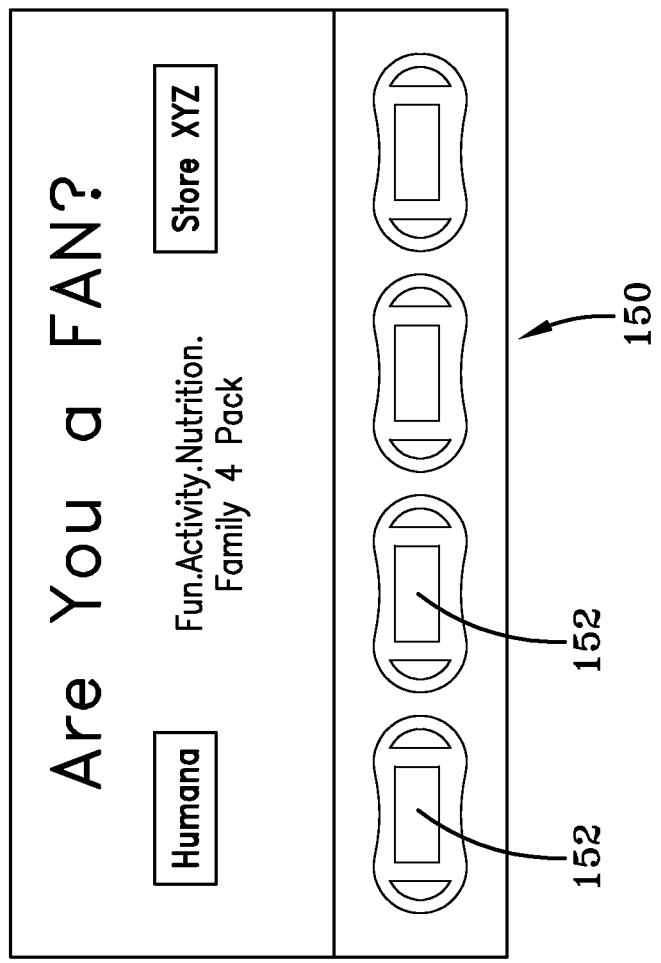
FIG. 7 is a sample kit of multiple pedometers sold for use with an example embodiment targeted towards family use.

In some embodiments the game may be played by family members in order to encourage physical activity and a healthy lifestyle at home. Referring to FIG. 7, a sample pedometer kit according to an example embodiment is shown. This kit 150 contains four pedometers 152 that can be used by a family or four other individuals. The kit 150 may also include software necessary for uploading data from the pedometers to the vendor's databases, USB cords or wireless routers for uploading data from the pedometer to a computer, and instructions on how to use the pedometers and participate in the on-line game. The kit may also include any other type of software, activity measurement device, or information necessary or helpful to playing the on-line game. While the kit shown in FIG. 7 is aimed to be used by four individuals, other kit embodiments may have more or fewer pedometers 152 and be targeted towards use with more or fewer than four people.

Figure 8:
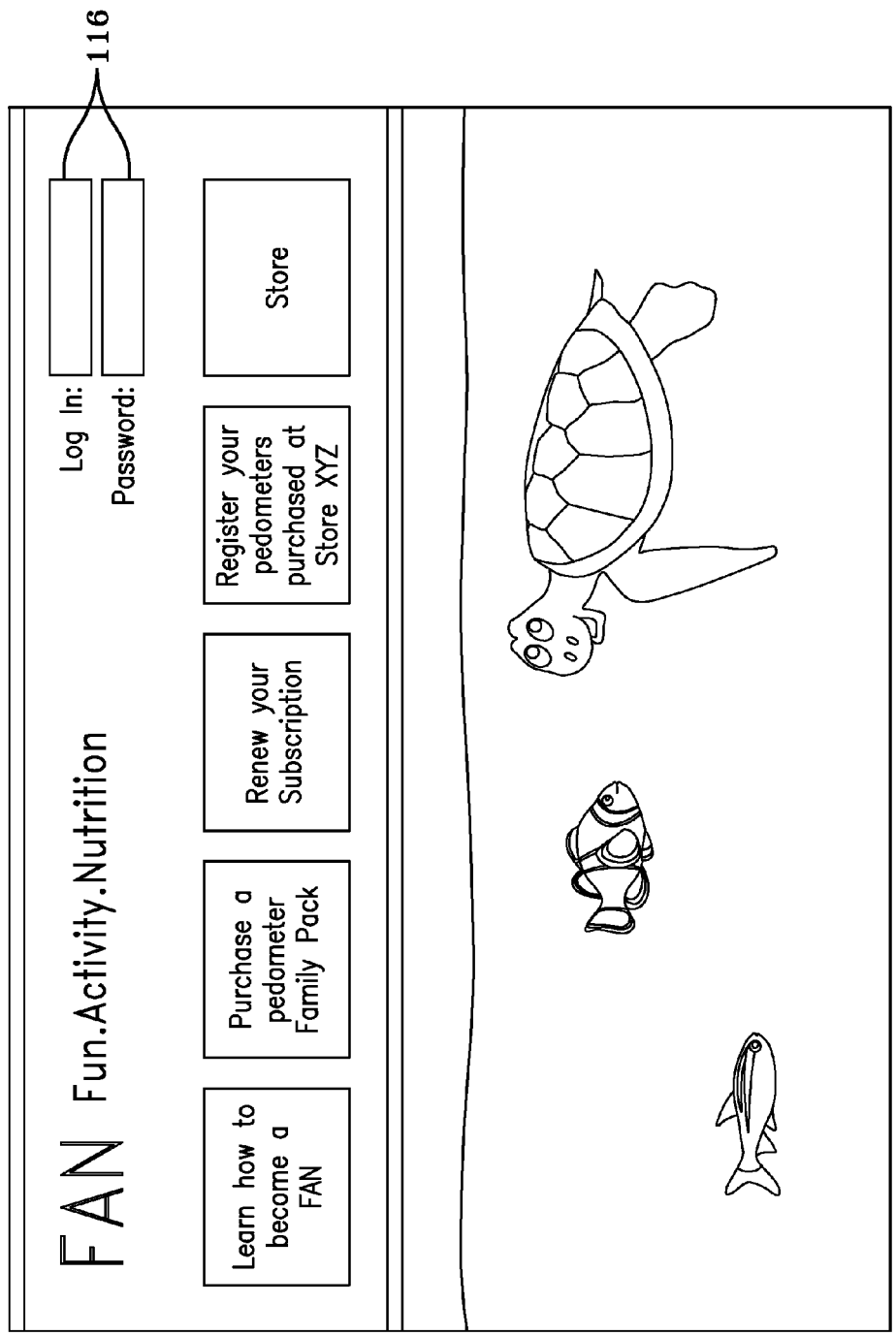
FIG. 8 is a sample log-in page according to an example embodiment targeted towards family use.

Referring to FIG. 8, a sample log-in page according to an example embodiment targeted towards family use is shown. This log-in page contains text boxes 116 for a user to provide their log in username and password in order to obtain entry into the game. Also, the log-in page contains various links to other pages that discuss different topics that may be of interest to someone playing the game.

Figure 9:
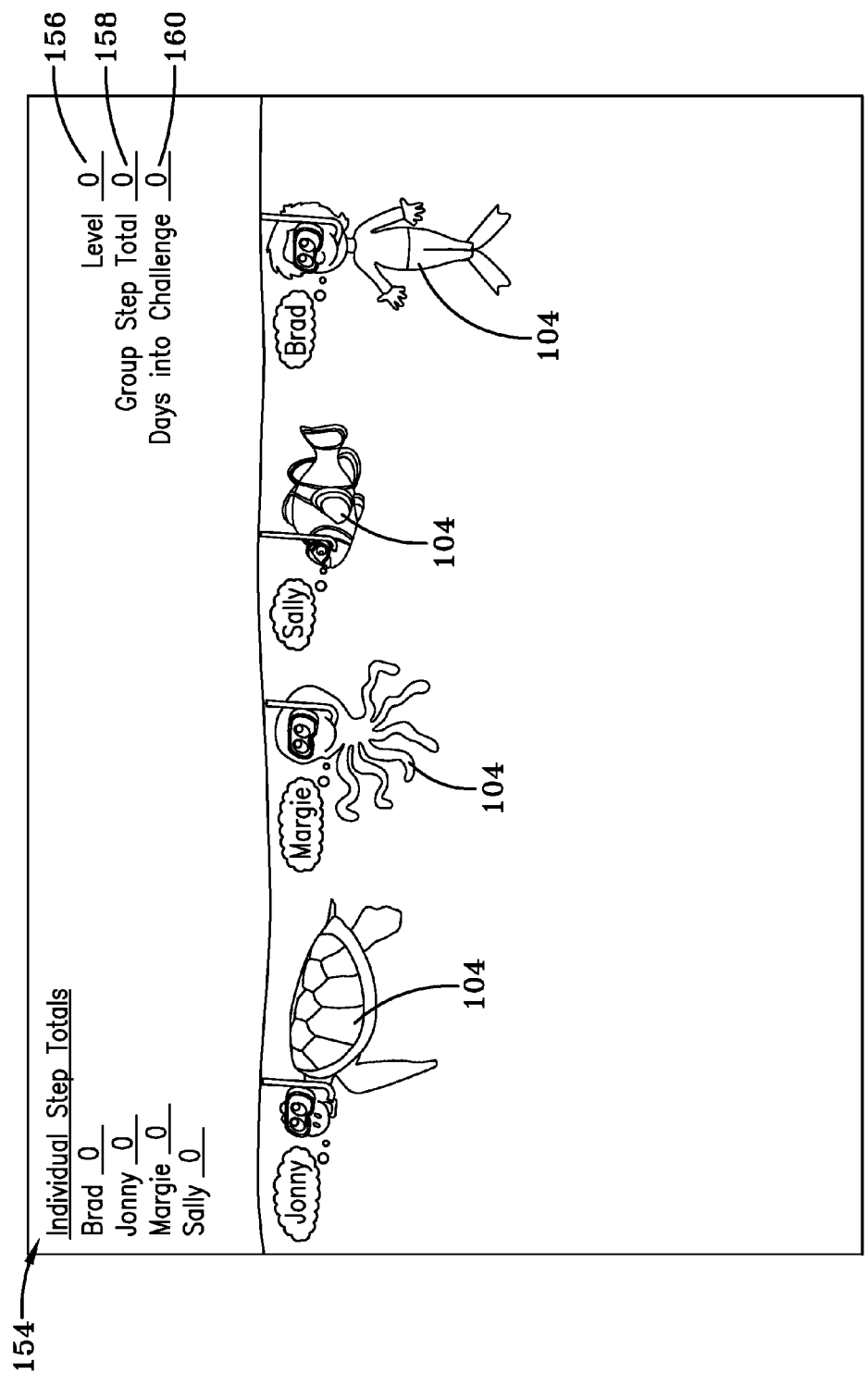
FIG. 9 is a sample fitness profile page according to an example embodiment of FIG. 8.

Referring to FIG. 9, a sample fitness profile page according to the example embodiment of FIG. 8 is shown. In this embodiment four avatars are associated with four different individuals. The avatars 104 are not all fish as in the embodiment shown in FIG. 1, but instead include a turtle, an octopus, and a person. This page includes a section for reporting step totals for each individual 154, and a section for reporting the level of the game 156, the group step total 158, and the days the group has been participating in the challenge 160. As shown in FIG. 9, it is day 0 of the game challenge, and all values for these items are 0.

Figure 10:
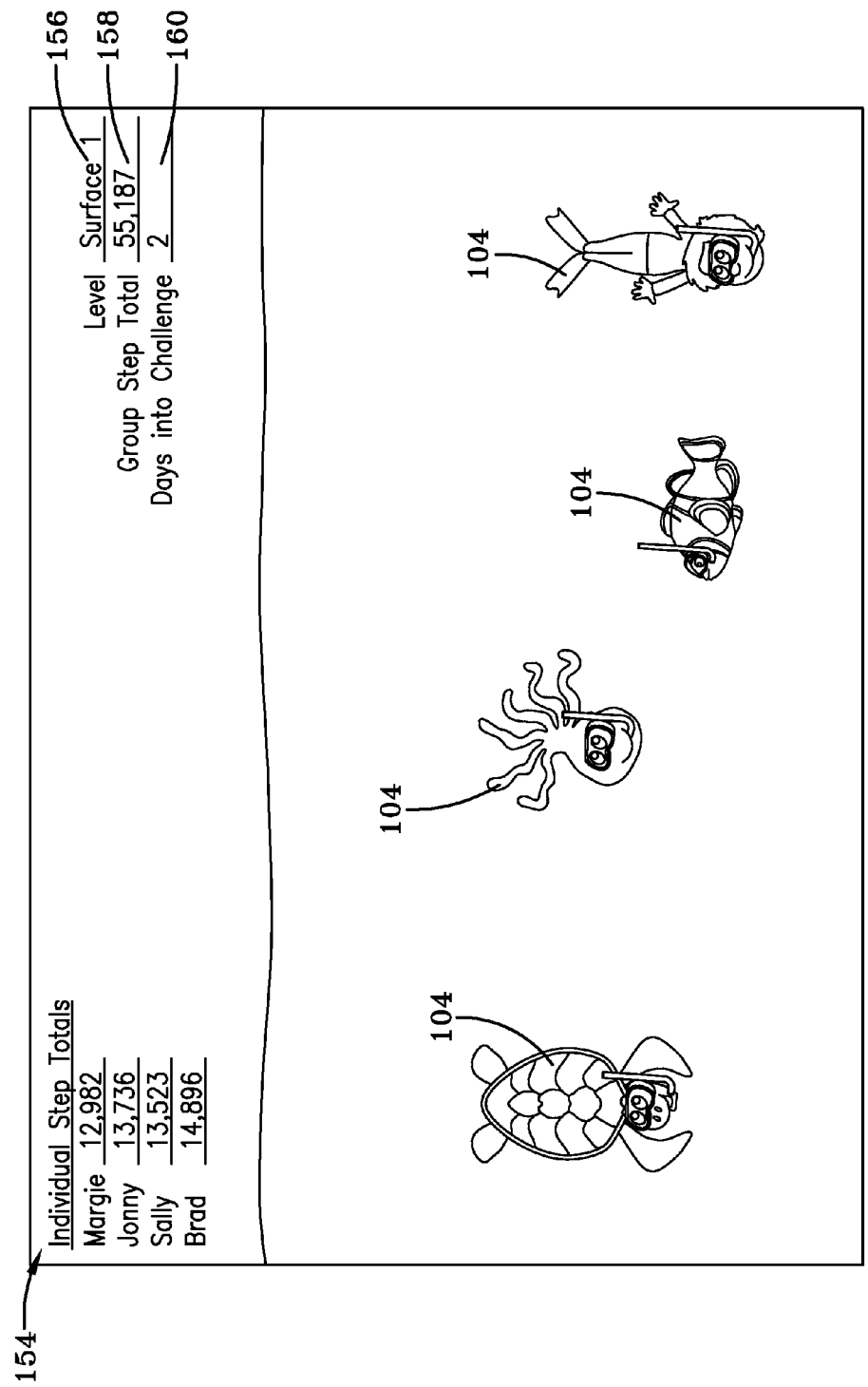
FIG. 10 is a sample fitness profile page according to an example embodiment targeted towards family use.

Referring to FIG. 10, a sample fitness profile page according to an example embodiment targeted towards family use is shown. This embodiment is the same as that shown in FIG. 9, except this page shows data received regarding the individuals. The individual step totals for the four individuals are set forth, as well as the game level, the total steps taken by the group, and the days into the challenge. As shown on this page, on the second day of this challenge the avatar 104 associated with the individual identified as Brad has taken the most steps. In this embodiment as individuals take more steps, they move farther down in the tank. Accordingly, Brad is positioned the lowest in the tank. Margie is the individual in this embodiment with the fewest steps taken, and her avatar 104 is positioned highest in the tank.

In an exemplary embodiment a user's activity levels are determined by pedometers that measure the number of steps the user takes throughout the day. Pedometers are commonly available in the market, and are made by many manufacturers including Sportline® Gaiam®, SportBrain® and FitLinxx®. Pedometers are typically carried by a person on their belt, waistband, or shoe for optimum accuracy. Vendors such as SportBrain® and FitLinxx® offer pedometers whose data can be uploaded to a computer and stored by the vendor in a data file corresponding to the user and available to the user online. Data from a pedometer may ether be directly uploaded to a computer via a USB connection, or may be uploaded automatically through a wireless connection made between the pedometer and a remote access point that is connected to the computer via a USB port.

Figure 11:
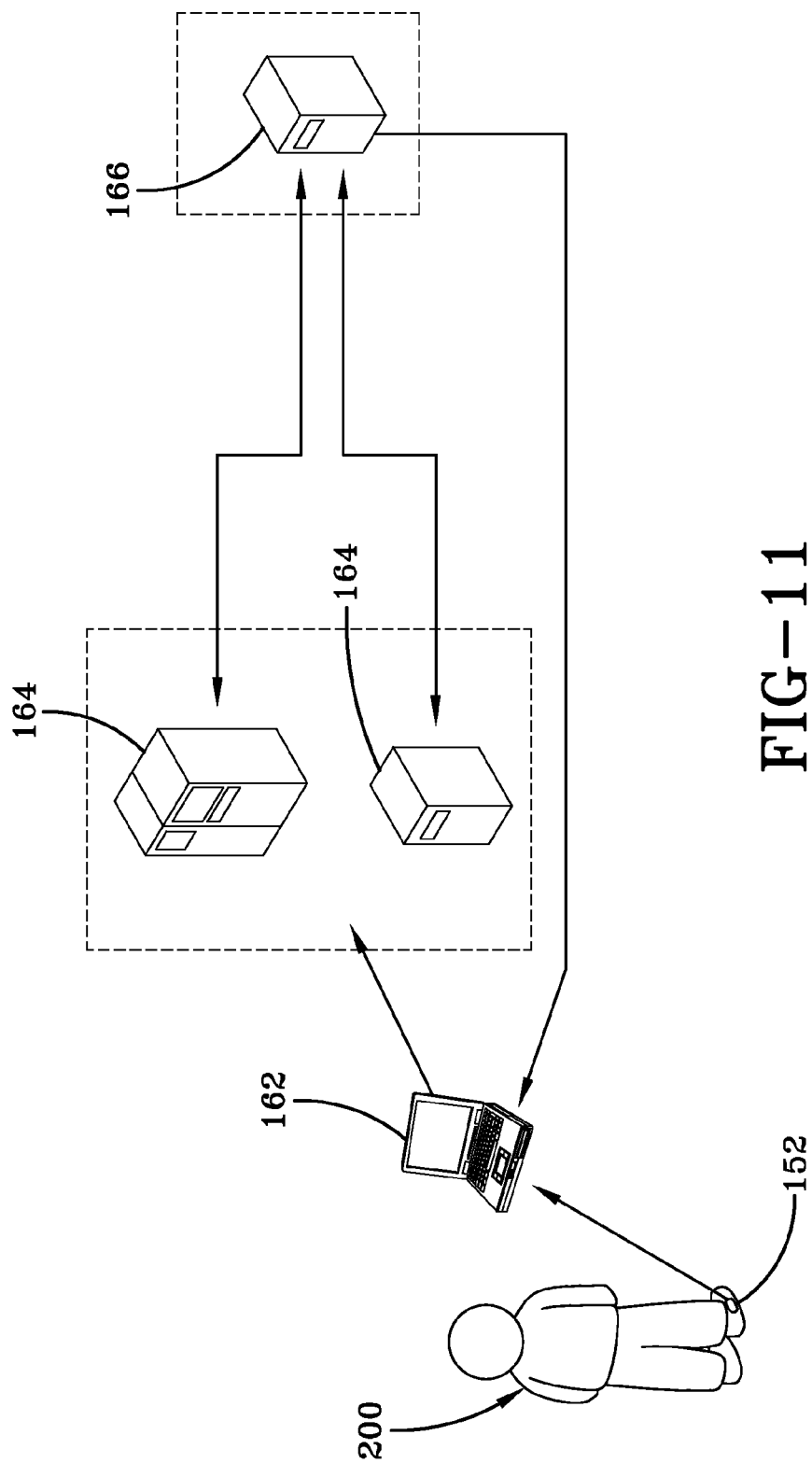
FIG. 11 is a diagram of hardware components to support user interaction with the system of an example embodiment.

Referring to FIG. 11, a block diagram of hardware components to support user interaction with the system of an example embodiment is shown. A user 200 is associated with a pedometer 152. The pedometer provides data about the user's activity level to a user computer 162. Data provided to the user computer 162 may include the number of steps the user 200 has taken, the distance traveled by the user, or other biometric information such as calories burned. The pedometer 152 may provide this data for a particular predetermined time period, or may send all data the pedometer 152 has acquired since its first use. Once the user computer has received this data, it sends the data to a remote data store 156. A remote data store 164 is a computer or group of computers separate from the user computer 162 that records and stores activity data for one or more users. Data sent from a user computer 162 to a remote data store 164 may be sent via the internet. Remote data stores 164 may include those data stores associated with Fitlinxx® and SportBrain® that record information sent by their brand of pedometers. The remote data store 164 stores data for different users in separate files, so that when queried it can send data pertaining to a particular user or users. A game application server 166 is a computer that runs the game application, including the creation of the game pages described above, and the web application associate with the game. Activity data used by the game application server 166 to run the game application is received from the remote data store 164 via the internet or a local network, as long as the remote data store 164 is accessible on the network. Software on the game application server 166 further supports the registration of users into the game, the selection of user profiles, and the calculations necessary to determine the relative positioning of avatars of different users in the game. For a game such as that shown in FIGS. 1-5, the game application server 166 performs the algorithms necessary to interpret the activity records of different users as the visual display of the fish tank.

In some embodiments the game application server 166 periodically queries one or more remote data stores 164 to update the activity level of a pre-defined set of users for the recent past. For example, the game application server 166 may query the remote data stores 164 every 24 hours in order to get daily updates on the activity level of its users. Similarly, the game application server 166 also periodically checks whether any user has updated his or her profile or changed the characteristics of the corresponding avatar. This information is received by the game application server 166 from the user computer 162 at which the change has been made. The game application server 166 stores changes as they are received so that when it performs its periodic updates such information is readily available. In some embodiments, when the game application server 166 updates user information the visualization automatically updates with the change, and it is not necessary to restart the game. For example, if a user changes the color of their fish avatar, the fish automatically changes color on all screens being viewed by different users at that time, without the need for the users to restart the game. In this way, a user can modify their avatar's appearance on one computer, such as a home computer, and their fish is automatically updated for everyone else watching the visualization of the fish tank on different screens. Depending on the network connection between the different user computers 162 and the game application server 166, there may be a short time delay between when an update is made on one computer until it is visible on other computer screens or touch screens.

In an embodiment as shown in FIGS. 1-5, the game application server 166 determines correlation and similarity in the activity level and activity timing of multiple users and provides a visual representation of the information by determining placement of the animated fish avatars 104 in the fish tank 100. The correlation and similarity is calculated by an algorithm which may consider the activity of each user over a particular time period, such as the past 24 hours, as an n-dimensional vector. The components of the vector may reflect the activity levels during pre-determined intervals throughout the day, such as 20 minute intervals. A unit vector for each user is computed, and a comparison matrix is calculated that contains the dot-product of every pair of users' unit vectors. These comparisons are then thresholded to decide on whether to group the pairs of users, and averaged n-dimensional unit vectors are then computed for each group made. Then the groups are then grouped, and the process continues recursively until a target group count is reached. The resultant groups of this algorithm are used to create "schools" of fish. Each school represents people with similar activity levels and timing. It may also be that the position of the individual fish, and by extension, of their schools in the tank is also a result of the similar activity level and timing of the users represented by the school. For example, in some embodiments those schools of fish swimming near the top of the tank may represent users who have higher activity levels than those in schools swimming near the bottom of the tank. In other embodiments the opposite may be true.

The diagram of FIG. 11 is only one embodiment of how the game system may be constructed. In some embodiments there may not be a remote data store, and once the user computer 162 receives data from the pedometer 152 it may upload the data directly to the game application server 166. In other embodiments the game application server 166 may be directly linked to remote access points that allow the game application server 166 to wirelessly upload data from a user's pedometer 152. For example, if the game is played among employees in a particular office there could be a single remote access point that wirelessly uploads information from different users' pedometers as they walk by.

Figure 12:
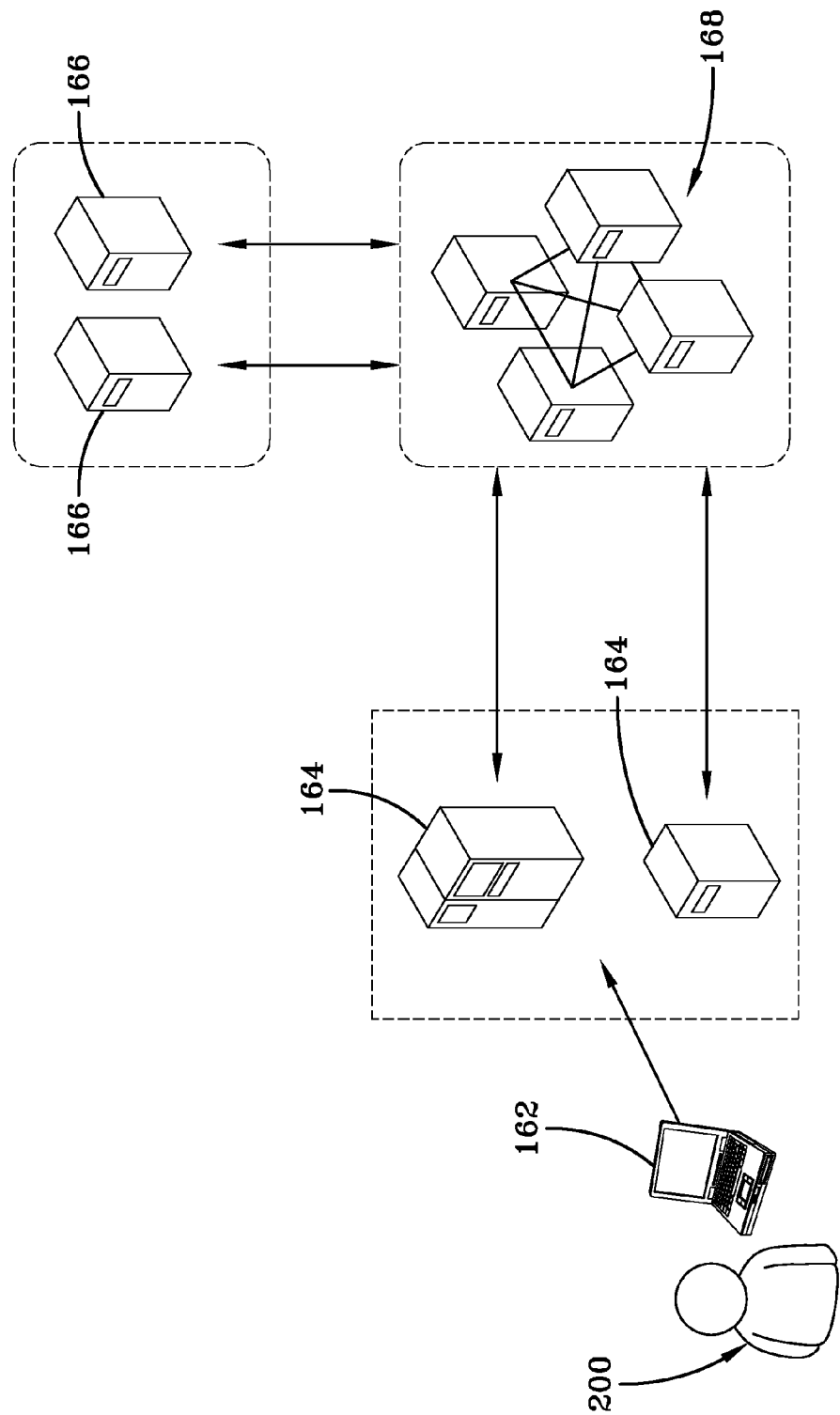
FIG. 12 is a diagram of hardware components to support user interaction with a system of an example embodiment.

In some embodiments data acquired from remote data stores 164 could be shared by two game application servers 166, which may be responsible for hosting different games. Referring to FIG. 12, a diagram of hardware components to support user interaction with the system of an example embodiment is shown, where a central computer 168 acts as an intermediary between the remote data stores 164 and the game application servers 166. In this way, activity data sent from multiple remote data stores can be collected by the central computer 168 and disseminated to multiple game application servers 166. This configuration may make it easier to integrate new data stores since it can reduce the need to alter game applications each time a new data store is added. Similarly, it may make it easier to make new devices work with older game applications. The central computer 168 may be a single computer, or multiple computers operating together via a common network.

Figure 13:
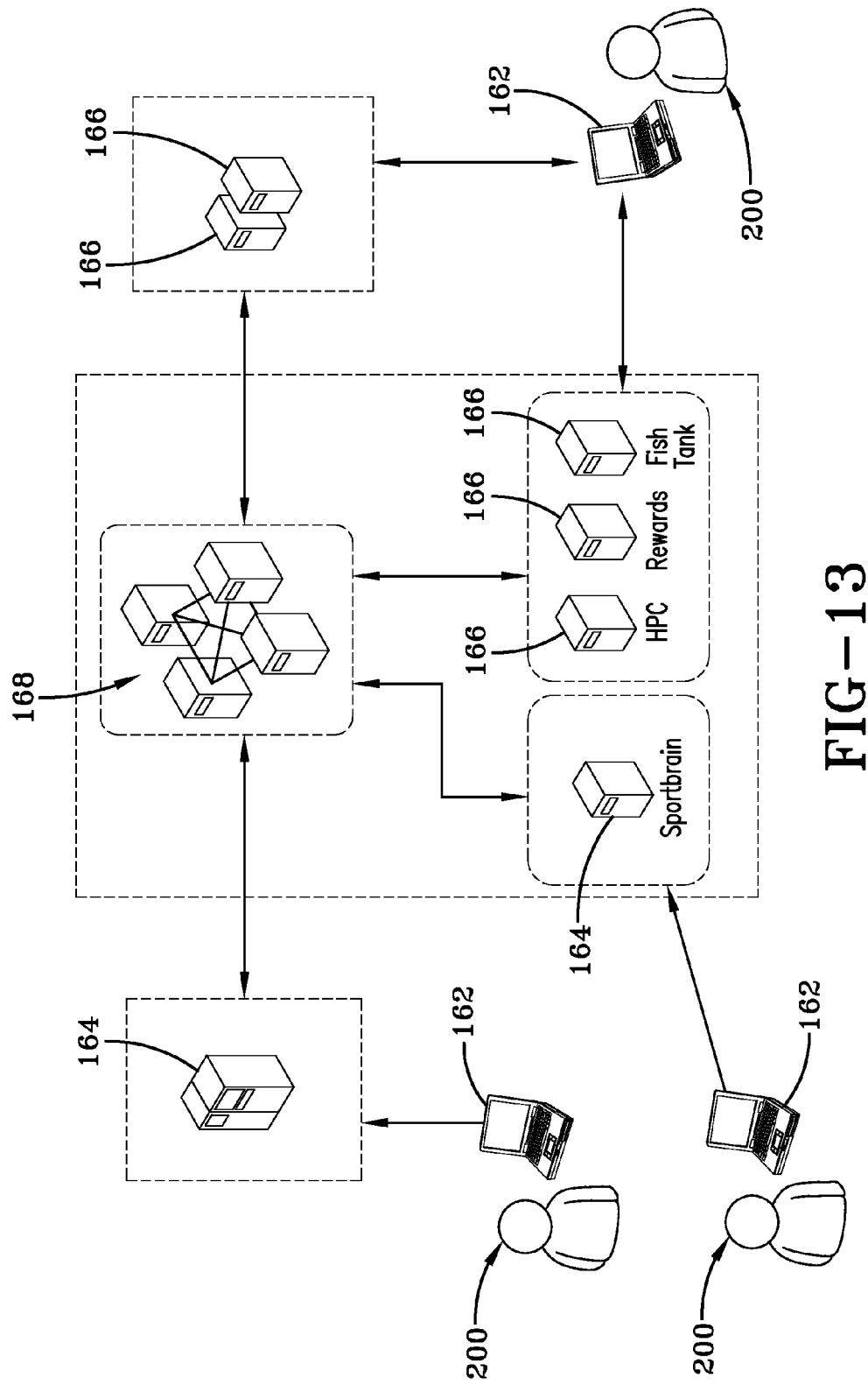
FIG. 13 is a diagram of hardware components to support user interaction with a system of an example embodiment.
Figure 14:
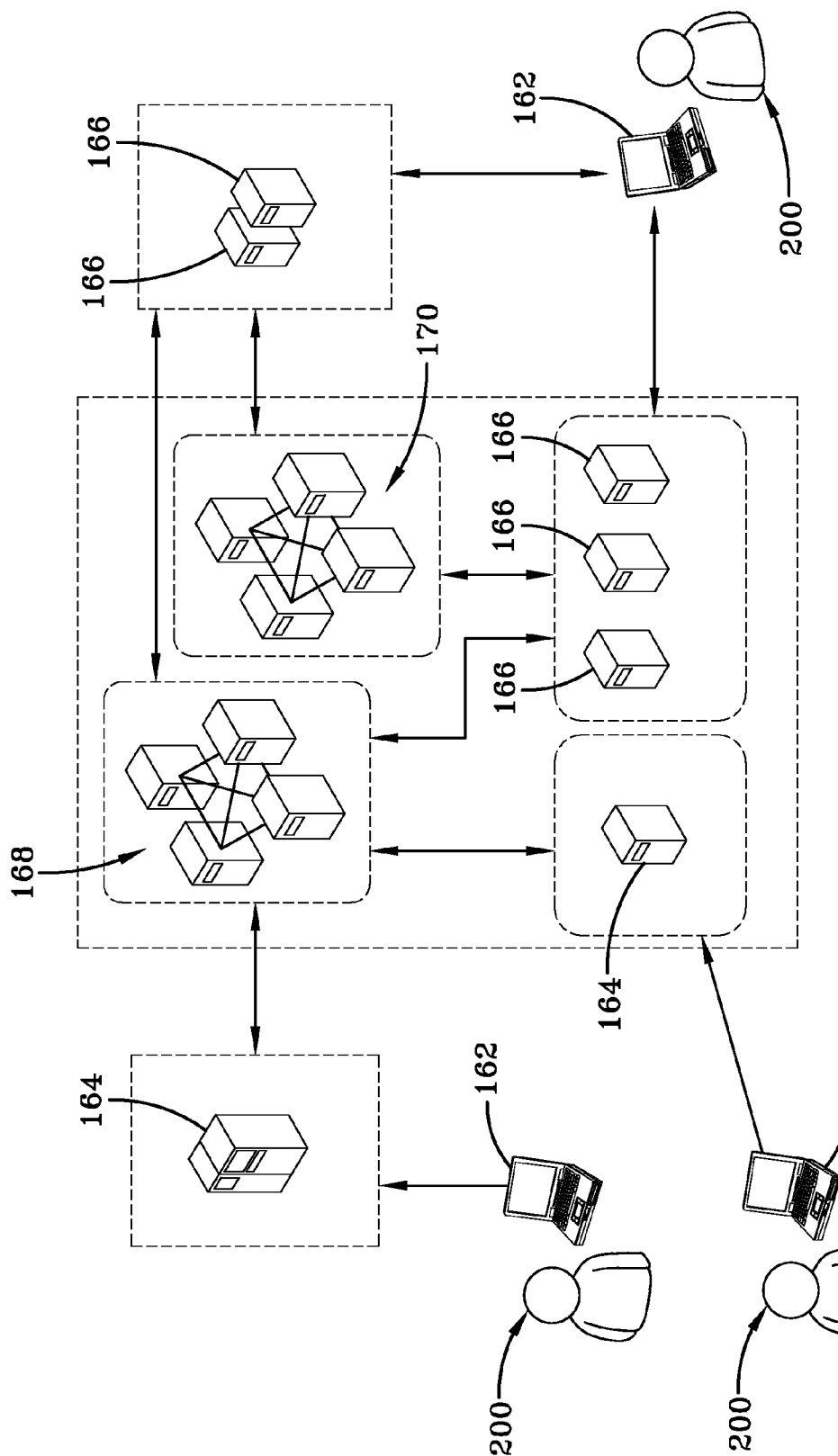
FIG. 14 is a diagram of hardware components to support user interaction with a system of an example embodiment.

Referring to FIGS. 13, and 14, a diagram of hardware components to support user interaction with the system of two different example embodiments are shown. In the embodiment shown in FIG. 14, the system includes a profile management system 170. The profile management system 170 stores the profiles of different users and related data. Different game applications run in the game application servers 166, which can attach arbitrary metadata to user profiles. Through the use of a profile management system, different game application servers 166 can read metadata from one another. With a profile management system 170 it may become possible to share avatars, biographies, and user preferences between different games, as well as for other types of cross-game interaction.

In an example embodiment, user biometric devices (e.g., pedometer) have firmware that communicates via a specified protocol over a USB to a synchronization software application executing on the user's computer. The synchronization software application then communicates via a specified protocol to a data store maintained by the device distributor. The protocols and related applications may be developed, documented, and published using Open Source products so that the data store is open to a variety of device manufacturers. As a result, the number of supported devices may be increased to facilitate participation of individuals using many different types of devices from many different manufacturers.

While the embodiments discussed in FIGS. 1-10 include an underwater theme with fish and other animals, other embodiments may have different themes. One possible theme is environmental, meaning that the more engaged a user is the more the environment changes. In some embodiments the ability to perform tasks in a visual environment may be dictated by the activity level of a user. One embodiment could take the form of building a beach resort and maintaining it for a period of time. In other embodiments different pieces of the environment may become unlocked or more defined to a user depending on their activity level, such as allowing the user to complete a puzzle or a painting.

In some embodiments the user's reward for activity is the evolution of their avatar. The avatar could either evolve in size, shape, or color, or the avatar may evolve into a completely different type of avatar depending on the activity of the user. For example, in some embodiments a player may start with a mouse avatar and depending on activity levels could evolve up to an elephant avatar.

In other embodiments the user's reward for activity would be some type of adventure for their avatar. The decisions regarding the adventure could be dictated by the user's activity levels.

Also, in some embodiments the activity that the game is based on may be different than just walking or something that is measured by a pedometer. Activities could include any type of action that can be measured and transmitted to the game. Also, the means for inputting a user's activity levels into the game could be accomplished through the use of biometric or other activity measurement devices, self-reported data, or a combination of both. Biometric devices may include pedometers, glucometers, weight scales, fitness equipment, or any other device capable of reporting biometric information about a user. Self-reported data may be necessary when the activity meant to be promoted by the game is not something that is easily measured by devices, such as behavioral goals. Examples of behavioral goals include caloric intake goals, and smoking cessation.

In some embodiments users may receive rewards for achieving a particular activity level. Rewards could be either actual rewards such as gifts, gift cards, store credit, discounts at participating stores, special offers, or experience packages. Rewards may also be virtual rewards that are simply fun to receive and show to other users, similar to those found in social networking games like Farmville, Restaurant City, or Mafia Wars that are often associated with Facebook™.

While certain embodiments of the present invention are described in detail above, the scope of the invention is not to be considered limited by such disclosure, and modifications are possible without departing from the spirit of the invention as evidenced by the claims. For example, other physical activities and related devices for measuring activity may be used and fall within the scope of the claimed invention. In addition, a variety of avatars may be used and fall within the scope of the claimed invention. One skilled in the art would recognize that such modifications are possible without departing from the scope of the claimed invention.

What is claimed is:

1. A computerized method for displaying data related to physical activity comprising:
   (a) storing at a server for each of a plurality of computer users:
      (1) a user identifier; and
      (2) an avatar;
   (b) receiving at said server for each of said plurality of computer users a plurality of biometric values;
   (c) calculating at said server for each of said plurality of computer users an activity value corresponding to said user's biometric values for a specified period of time;
   (d) correlating said activity values of said plurality of computer users to define a plurality of activity groups, each of said activity groups comprising a target group count of users with similar activity values;
   (e) transmitting from said server to a computer display said avatar for each of said plurality of users; and
   (f) transmitting from said server to said computer display animation data to:
      (1) place said avatars in each activity group on said computer display; and
      (2) move around said computer display said avatars in each activity group according to said correlated activity values for each of said activity groups.

2. The computerized method of claim 1 wherein transmitting from said server to said computer display animation data comprises transmitting animation data to simulate swimming.

3. The computerized method of claim 2 wherein storing at said server an avatar for said user comprises storing a fish avatar.

4. The computerized method claim 1 further comprising:
   (g) receiving at said server a user's selection of an avatar appearing on said computer display;
   (h) in response to receiving said user's selection of an avatar, displaying a biometric value for said computer user associated with said avatar.

5. The computerized method of claim 1 wherein said biometric value is received from a device selected from the group consisting of:
   pedometers, glucometers, and weight scales.

6. The computerized method of claim 1 further comprising receiving from one of said plurality of computer users a selection of a different avatar.

7. The computer method of claim 6 wherein receiving from one of said plurality of computer users a selection of a different avatar comprises receiving a selection of an avatar type, an avatar size, and an avatar color.

8. The computerized method of claim 1 further comprising receiving from one of said plurality of computer users a request to view said computer user's biometric values over said specified period of time.

9. The computerized method of claim 1 further comprising:
   (g) receiving from said plurality of computer users updated biometric values;
   (h) regrouping said avatars on said computer display according to new activity values calculated from said updated biometric values; and
   (i) transmitting to said computer display animation data to:
      (1) visually regroup said avatars; and
      (2) animate said avatars in new activity groups according to said new activity values.

10. A computerized method of claim 1 wherein said display is a touch screen.

11. A computerized system for displaying data related to physical activity comprising:
   (a) a computer database for storing for each of a plurality of computer users:
      (1) a user identifier;
      (2) an avatar; and
      (3) a plurality of biometric measurements for an activity time period;
   (b) a server in communication with said computer database for:
      (1) calculating for each of said plurality of computer users an activity value corresponding to said user's biometric measurements;
      (2) defining a plurality of activity groups by comparing said computer users' activity values to identify users with correlated activity values;
      (3) adding computer users with correlated activity values to one of said activity groups until a target group count is reached;
      (4) transmitting to a computer display:
         (A) said avatar for each of said plurality of users; and
         (B) animation data to:
            (i) place said avatars in each activity group on said computer display; and
            (ii) move around said computer display said avatars in each activity group according to said correlated activity values for each of said activity groups.

12. The computerized system of claim 11 wherein said animation data comprises animation data to simulate swimming.

13. The computerized system of claim 11 wherein storing an avatar for said user comprises storing a fish avatar.

14. The computerized system of claim 11 wherein said server further:
   (5) receives a user's selection of an avatar appearing on said computer display; and
   (6) in response to receiving said user selection, displays a biometric measurement for said selected avatar.

15. The computerized system of claim 11 wherein said biometric measurements are from devices selected from the group consisting of:
   pedometers, glucometers, and weight scales.

16. The computerized system of claim 11 wherein said computer display is a touch screen.

17. A computerized method for displaying data related to physical activity comprising:
   (a) storing at a server for each of a plurality of computer users:
      (1) a user identifier; and
      (2) an avatar;
   (b) receiving at said server for each of said plurality of computer users a plurality of biometric values;
   (c) calculating at said server for each of said plurality of computer users an activity value corresponding to said user's biometric values;
   (d) defining at said server a plurality of activity groups by:
      (1) correlating said computer users' activity values to identify users with similar activity levels; and
      (2) adding computer users with similar activity values to one of said plurality of activity groups until a target group count for said group is reached;
   (e) transmitting from said server to a computer display said avatar for each of said plurality of users; and
   (f) transmitting from said server to said computer display animation data to:

(1) place said avatars in each activity group on said computer display; and
(2) move around said computer display said avatars in each activity group according to said correlated activity values for each of said activity groups.

18. The computerized method of claim 17 wherein said avatars are animated in activity groups at varying heights, directions, and speed.

19. The computerized method of claim 17 wherein said plurality of biometric values are received over a defined time period.

20. The computerized method of claim 17 wherein said biometric values are from devices selected from the group consisting of:
pedometers, glucometers, and weight scales.

* * * * *